(12) United States Patent
Hartmann et al.

(10) Patent No.: US 8,367,347 B2
(45) Date of Patent: Feb. 5, 2013

(54) METHODS FOR THE DIAGNOSIS AND THE PROGNOSIS OF A BRAIN TUMOR

(75) Inventors: Christian Hartmann, Lorsch (DE); Andreas von Deimling, Schriesheim (DE); Hanswalter Zentgraf, Heidelberg (DE); David Capper, Heidelberg (DE); Guido Reifenberger, Düsseldorf (DE); Michael Weller, Männedorf (CH); Wolfgang Wick, Heidelberg (DE)

(73) Assignee: Deutsches Krebsforschungszentrum Stiftung des Offentlichen Rechts and Ruprecht-Karls-Univeristat Heidelberg (DE)

( * ) Notice: Subject to any disclaimer, the term of this patent is extended or adjusted under 35 U.S.C. 154(b) by 152 days.

(21) Appl. No.: 12/637,233

(22) Filed: Dec. 14, 2009

(65) Prior Publication Data

US 2010/0291590 A1 Nov. 18, 2010

(30) Foreign Application Priority Data

May 15, 2009 (EP) .................................... 09006620

(51) Int. Cl.
*G01N 33/53* (2006.01)
*C07K 16/00* (2006.01)
*C12P 21/08* (2006.01)

(52) U.S. Cl. ................ 435/7.1; 530/388.15; 530/387.3
(58) Field of Classification Search ...................... None
See application file for complete search history.

(56) References Cited

U.S. PATENT DOCUMENTS 6,153,603 A * 11/2000 Siren ............................. 514/102
2002/0165349 A1 * 11/2002 Kirsch et al. ................... 530/350

FOREIGN PATENT DOCUMENTS
WO 2010028099 3/2010

OTHER PUBLICATIONS

Turner et al., J. Clin. Oncol. 2001, 19(4): 992-1000.*
Tang et al., J. Clin. Oncol. 1999, 17(6): 1710-1719.*
Krajewska et al., Prostate, 2006, 66:801-810.*
Balss, Jorg et al. "Analysis of the IDH1 codon 132 mutation in brain tumors." Acta Neuropathol (2008) 116:597-602.
Kang, Mi Ran et al. "Mutational analysis of IDH1 codon in glioblastomas and other common cancers." Int. J. Cancer: 125: 353-355 (2009).
Parsons, D. Williams et al. "An Integrated Genomic Analysis of Human Glioblastoma Multiforme." Science, vol. 321, Sep. 26, 2008, pp. 1807-1812.
Watanabe, Takuya et al. "Selective acquisition of IDH1 R132C mutations in astrocytomas associated with Li-Fraumeni syndrome." Acta Neuropathol (2009) 117:653-656.
Watanabe, Takuya et al. "IDH1 Mutations are Early Events in the Development of Astrocytomas and Oligodendrogliomas." AJP Apr. 2009, vol. 174, No. 4, pp. 1149-1153.
Yan, Hai et al. "IDH1 and IDH2 Mutations in Gliomas." N Engl J Med 2009;360:765-773.
Zhao, Shimin et al. "Glioma-Derived Mutations in IDH1 Dominantly Inhibit IDH1 Catalytic Activity and Induce HIF-1α." Science, vol. 324, Apr. 10, 2009, pp. 261-265.

* cited by examiner

*Primary Examiner* — Hong Sang
(74) *Attorney, Agent, or Firm* — Marianne Fuierer; Moore & Van Allen, PLLC

(57) ABSTRACT

The present invention relates to methods for the diagnosis of a brain tumor and for the estimation of a prognosis for patients having a brain tumor using the presence/absence of a particular IDH1 mutation as a marker.

9 Claims, 3 Drawing Sheets

SEQUENCE LISTING

```
<160> NUMBER OF SEQ ID NOS: 1

<210> SEQ ID NO 1
<211> LENGTH: 13
<212> TYPE: PRT
<213> ORGANISM: Artificial Sequence
<220> FEATURE:
<223> OTHER INFORMATION: Synthetic construct

<400> SEQUENCE: 1

Cys Lys Pro Ile Ile Ile Gly His His Ala Tyr Gly Asp
1               5                   10
```

US 8,367,347 B2

METHODS FOR THE DIAGNOSIS AND THE PROGNOSIS OF A BRAIN TUMOR

CROSS REFERENCE TO RELATED APPLICATIONS

This application claims priority to European Patent Application No. 09 006 620.0 filed on May 15, 2009, the contents of which are incorporated by reference herein for all purposes.

BACKGROUND OF THE INVENTION

1. Technical Field

The present invention relates to methods for the diagnosis of a brain tumor and for the estimation of a prognosis for patients having a brain tumor using the presence/absence of a particular IDH1 mutation as a marker.

2. Related Art

Cancer is the second leading cause of death in the United States after cardiovascular disease. One in three Americans will develop cancer in his or her lifetime, and one of every four Americans will die of cancer. Malignant human gliomas account for the largest number of human malignant brain tumors. So far, the treatment of gliomas includes neurosurgical techniques (resection or stereotactic procedures), radiation therapy and chemotherapy. However, despite these therapies gliomas are considered as nearly incurable as they fail to respond to ionising radiation, chemotherapy and surgical resection. In other words, with these therapies only a very limited prolongation of lifespan of patients can be achieved, i.e. despite these therapies, the average life span after diagnosis is merely 12 to 16 months. The knowledge of prognostic factors might be decisive for the selection of the preferable kind of life prolonging therapy.

SUMMARY OF THE INVENTION

The technical problem underlying the present invention is to provide diagnostic methods for a brain tumor and for providing an overall survival or progression prognosis for patients having a brain tumor, leading to a distinct decision of a physician for a particular kind of treatment.

The solution to said technical problem is achieved by providing the embodiments characterized in the claims.

Thus, the present invention relates to methods for the diagnosis and for the estimation of a prognosis for patients having a brain tumor using the presence/absence of a particular IDH1 mutation as a prognostic marker. In this method, the presence of a mutation at preferably position 132 of isocitrate dehydrogenase (IDH1) is determined on the protein level using an antibody that can distinguish between an IDH1 protein harbouring said mutation and an unmutated version of the protein.

Mutations in the gene encoding cytosolic NADP+ dependent isocitrate dehydrogenase (IDH1) emerged as an unsuspected finding in sequence analysis of glioblastoma (GBM) [Parsons et al., Science. 2008 Sep. 26; 321(5897):1807-12]. Recent studies reported on mutations in the IDH1 gene resulting in an amino acid exchange in position 132 in about 70% of anaplastic gliomas and 12% of glioblastomas [Balls et al., Acta Neuropathol. 2008 December; 116(6):597-602, Yan et al., N Engl J. Med. 2009 Feb. 19; 360(8):765-73, Watanabe et al., Am J Pathol. 2009 April; 174(4):1149-53, De Carli et al., N Engl J. Med. 2009 May 21; 360(21):2248, Ducray et al., N Engl J. Med. 2009 May 21; 360(21):2248, Hartmann et al., Acta Neuropathol. 2009 October; 118(4):469-74, Ichimura et al., Neuro Oncol. 2009 August; 11(4):341-7, Sanson et al., J Clin Oncol. 2009 Sep. 1; 27(25):4150-4, Weller et al., J Clin Oncol. 2009 Oct. 5, Wick et al., J Clin Oncol. 2009 Nov. 9]. Isocitrate dehydrogenase catalyzes the oxidative decarboxylation of isocitrate to alpha-ketoglutarate thereby reducing NADP+ to NADPH. Mutations affected the amino acid arginine in position 132 of the amino acid sequence which belongs to an evolutionary conserved region located to the binding site of isocitrate. The mutations reported always were heterozygous and alterations suggestive for protein inactivation, such as splice site or nonsense mutations, were not detected, thus prompting speculations on an activating nature of the mutation. However, the measurement of enzymatic activity showed an inactivating effect of the mutation [Yan et al., N Engl J. Med. 2009 Feb. 19; 360(8):765-73]. As a consequence induction of HIF1alpha was described [Zhao et al., Science. 2009 Apr. 10; 324(5924):261-5]. In addition, IDH1 mutation result in a new ability to catalyze alpha-ketogluterate to 2-hydroxygluterate [Dang et al., Nature. 2009. Nov. 22, doi:10.1038/nature08617].

IDH1 mutations occur in a high frequency in WHO grade II and III diffuse gliomas. 93% of all IDH1 mutations are characterized by an amino acid exchange R132H [Hartmann et al., Acta Neuropathol. 2009 October; 118(4):469-74]. The present invention is based on a study involving a series of about 220 anaplastic gliomas WHO grade III which are part of an NOA-04 study (randomized phase-III-study of sequential radiochemotherapy of oligoastrocytomas WHO grade III using PCV or temozolomide), for IDH1 mutation [Wick et al., J Clin Oncol. 2009 Nov. 9].

Finally, to date the diagnostic analysis of an IDH1 mutation is carried out on the DNA level which is problematic. Some of the major problems are: (a) insufficient material for DNA extraction, (b) lack of a molecular laboratory at all in most departments of pathology, and (c) the need for a short time frame from tumor resection to the begin of the adjuvant therapy.

The antibody of the present invention described in more detail below overcomes these problems since it allows a fast, simple and reliable analysis of the IDH1 status by immunohistochemistry, i.e., the detection of the IDH1 mutation can be performed in any department of pathology, results can be generated faster, and the reliability is ensured since in opposite to gene analysis also individual tumor cells within other unconspicuous tissue can be detected even in the case that the quality of the tumor tissue sample is poor.

(B) On the same blot both, wild type and mutant IDH1 is detected by antibody rIDH1 in the same lysates 1 to 5.

Figure 3:
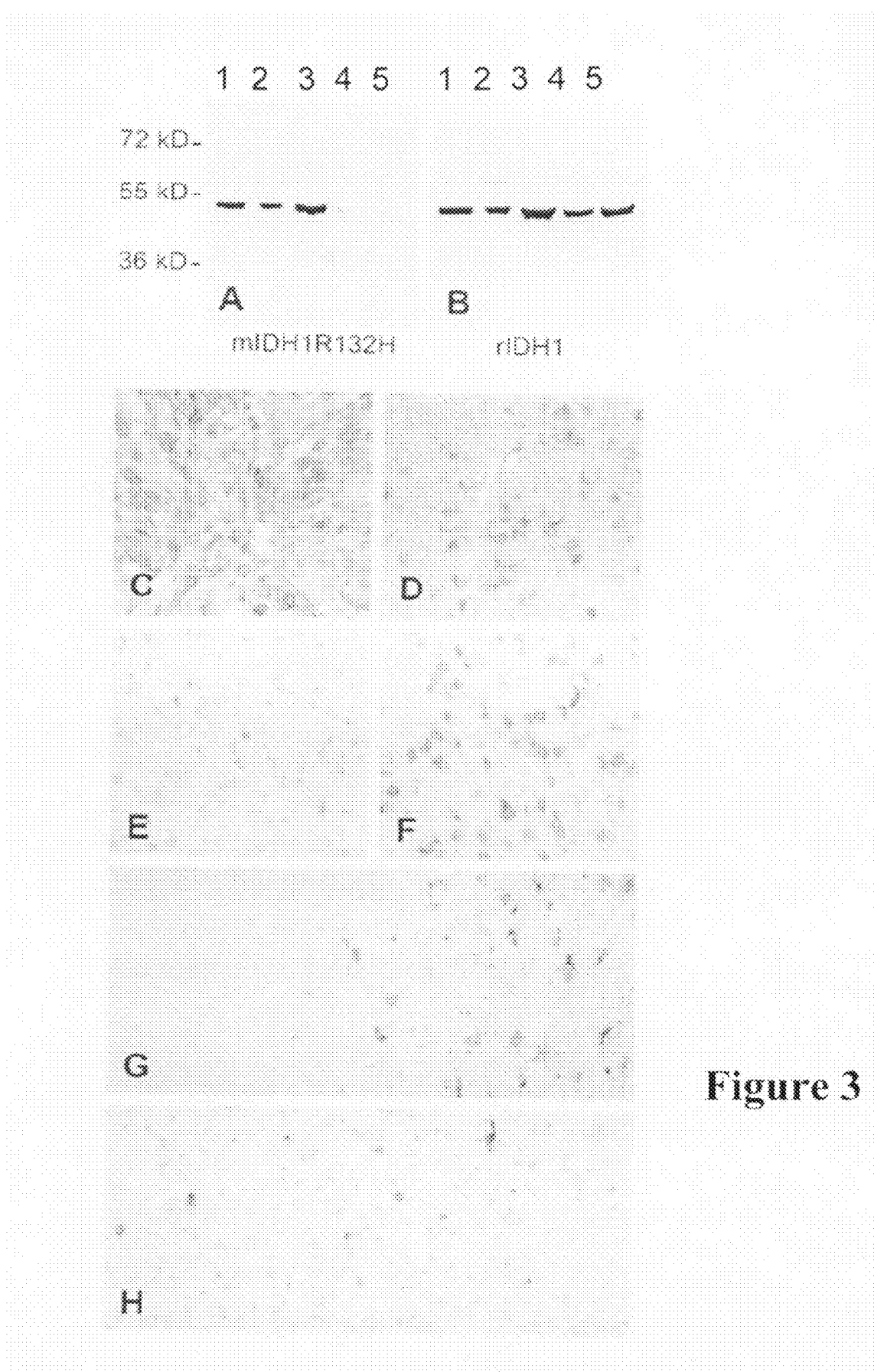
FIG. 3: (A) Western Blot showing binding of R132H mutation specific deposited antibody mIDH1R132H. Lysates in lanes 1 (ID 40954), 2 (ID 41560) and 3 (ID 41402) are from 3 different gliomas carrying the IDH1 R132H mutation, lysate in lane 4 (ID 41654) is from a glioma with wild type IDH1 sequence and lysate in lane 5 (ID 41522) is from a glioma with R132C mutation. mIDH1 R132H detects antigen exclusively in gliomas carrying the IDH1 R132H mutation.

(C) Binding of mIDH1R132H to formalin fixed paraffin embedded tissue from ID 40954 (corresponding to lane 1 in FIGS. 3 A, B).

(D) Binding of mIDH1R132H to ID 41402 (lane 3).

(E) No binding of mIDH1R132H to ID 41654 (lane 4).

(F) Binding of rIDH1 to ID 41654 (lane 4).

(G) Binding of mIDH1R132H to ID 43906 at the infiltration edge to cortex.

(H) Binding of mIDH1 R132H to ID 43906 at the infiltration edge to white matter.

DETAILED DESCRIPTION OF THE INVENTION

The present invention relates to a diagnostic method for the estimation of a prognosis for patients having a brain tumor, comprising
 (a) obtaining a brain tumor sample from a patient; and
 (b) determining the presence of a mutation at position 132 of isocitrate dehydrogenase (IDH1) on the protein level using an antibody that can distinguish between an IDH1 protein harbouring said mutation and an unmutated version of the protein;
whereby a patient harbouring said mutation has a better prognosis than a patient without said mutation.

In an alternative embodiment, the present invention relates to a method of selecting a therapy modality for a patient afflicted with a brain tumor, comprising
 (a) obtaining a brain tumor sample from said patient; and
 (b) determining the presence of a mutation at position 132 of isocitrate dehydrogenase (IDH1) on the protein level using an antibody that can distinguish between an IDH1 protein harbouring said mutation and an unmutated version of the protein;
 whereby the selection of a therapy modality depends on the presence or absence of said mutation.

In a further alternative embodiment the invention concerns a method of diagnosing a brain tumor in a patient suspected of having a brain tumor, comprising
(a) obtaining a brain sample suspected of harboring a tumor from said patient; and
(b) determining the presence of single tumor cells within otherwise inconspicuous tissue by using an antibody that specifically binds to an isocitrate dehydrogenase (IDH1) protein harbouring a mutation at position 132.

The term "prognosis" concerns an estimation of the overall survival time in months.

The term "brain tumor sample" or "brain sample" as used herein, refers to a sample obtained from a patient. The brain (tumor) sample can be obtained from the patient by routine measures known to the person skilled in the art, i.e., biopsy (taken by aspiration or punctuation, excision or by any other surgical method leading to biopsy or resected cellular material). For those areas not easily reached via an open biopsy, a surgeon can, through a small hole made in the skull, use stereotaxic instrumentation to obtain a "closed" biopsy. Stereotaxic instrumentation allows the surgeon to precisely position a biopsy probe in three-dimensional space to allow access almost anywhere in the brain. Therefore, it is possible to obtain tissue for the diagnostic method of the present invention.

The term "brain tumor" is not limited to any stage, grade, histomorphological feature, invasiveness, agressivity or malignancy of an affected tissue or cell aggregation. In particular grade I, grade II, grade III or grade IV brain tumors, and all other types of cancers, malignancies and transformations associated with the brain are included. A preferred brain tumor to be diagnosed by the method of the present invention is a glioma. Preferred are anaplastic astrocytomas, anaplastic oligoastrocytomas and anaplastic oligodendrogliomas, in particular fibrillary astrocytoma WHO grade II, oligoastrocytoma WHO grade II, oligodendroglioma grade II, anaplastic astrocytoma WHO grade III, anaplastic oligoastrocytoma WHO grade III, anaplastic oligodendroglioma grade III or glioblastoma.

Figure 2:
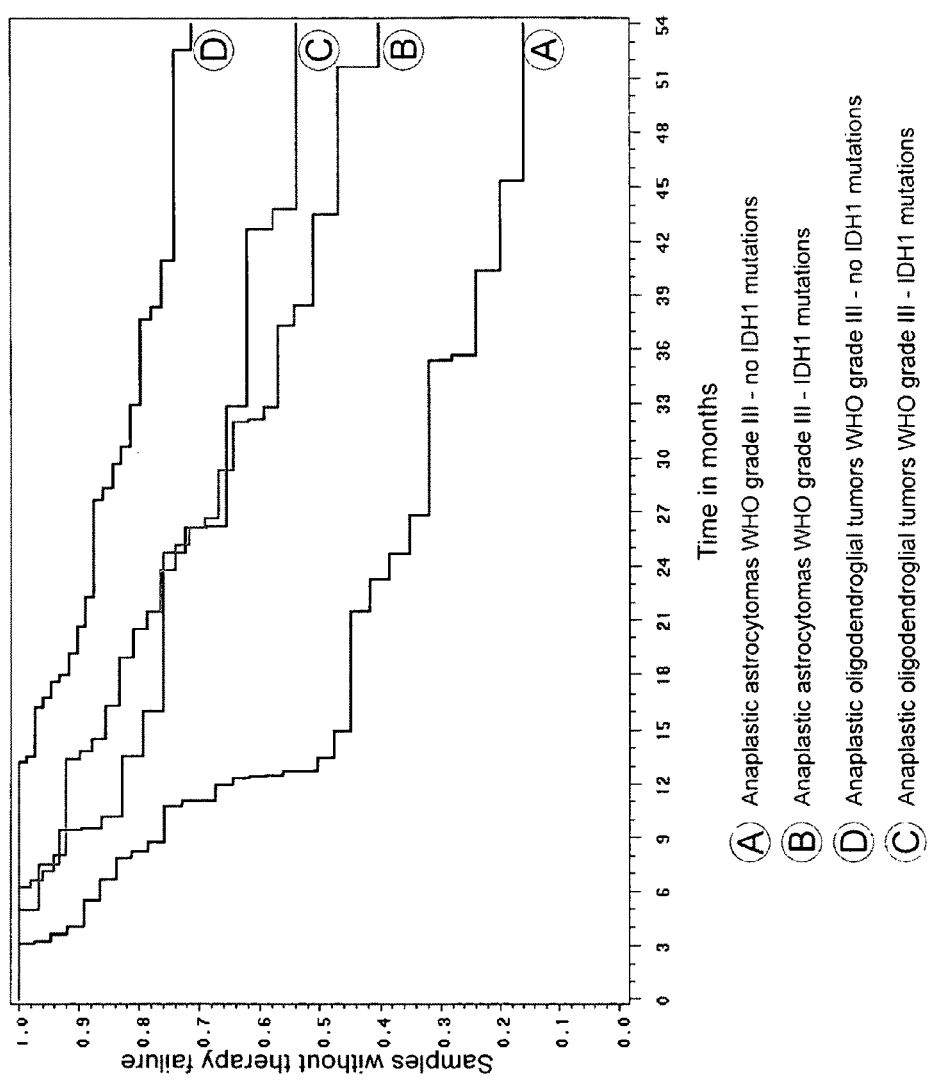
FIG. 2: Survival of patients with tumors with and without IDH1 mutations based on the NOA-04 study. For details, see Example 4.

The term "better prognosis than a patient without said mutation" as used herein means that the probability of having a given remaining expectancy of life is increased by a factor of at least 1,4, preferably of at least 2,5 (cf. the results presented in FIG. 2). For example, in case of anaplastic astromcytomas WHO grade III the 54 months survival rate for patients having no IDH1 mutation is about 16% whereas the survival rate for patients having the IDH1 mutation is about 40%.

Unexpectedly, it could be demonstrated that patients harbouring IDH1 mutations have a better prognosis compared to patients without an IDH1 mutation. This effect was found to be independent from other established molecular markers like losses on 1p/19q and methylation of the MGMT promoter. This observation shows that the analysis of the IDH1 status is of great interest in the field of neurooncology and is useful as a prognostic or predictive marker. Moreover, it can be expected that the knowledge of the IDH1 status has consequences for decisions of the attending physician regarding the particular kind of treatment of patients with (diffuse) gliomas. The prognosis of anaplastic astrocytomas WHO grade III without IDH1 mutations is more or less identical to the prognosis of glioblastomas WHO grade IV. Knowing the IDH1 status attending physicians will treat those anaplastic astrocytomas WHO grade III without IDH1 mutations with the same protocols that are applied to patients with glioblastomas. Instead, patients with anaplastic astrocytomas WHO grade III with IDH1 mutations will be treated with a less radical adjuvant therapy. For example, the NOA (Neuroonkologic Working Committee (Neuroonkologische Arbeitsgemeinschaft); guidelines for patients with anaplastic astrocytomas WHO grade III recommend combined radiotherapy (up to 65 Gy) and chemotherapy (TMZ or PZV) only for patients below 40 years of age. However, for patients with glioblastomas WHO grade IV this age cutoff is set to 65 years. Knowing the IDH1 mutation status it is likely that patients with anaplastic astrocytomas WHO grade III and no IDH1 mutation will be treated with combined radio- and chemotherapy even if they are older than 40 years, similar to patients with glioblastomas.

In a preferred embodiment of the methods of the present invention the IDH1 mutation to be screened is the mutation R132H (corresponding to G395A on the nucleic acid sequence level).

The mutation can be assayed by standard methods known to the person skilled in the art. The nucleic acid sequence and derived amino acid sequence of IDH1 have been published (Parsons et al., Science 2008, 321(5897): 1807-1812; Balss et al., Acta Neuropathol. 2008, 116(6): 597-602).

Preferred assays use an antibody that specifically binds (a) to an IDH1 protein harbouring said mutation or (b) to an epitope of the unmutated version of the protein. The approach (a) is preferred because in opposite to gene analysis it is possible to detect individual tumor cells within otherwise unconspicuous tissue. Such an antibody can be generated using the IDH1 derived peptide CKPIIIGHHAYGD (SEQ ID NO: 1) as an immunogen. A particular preferred antibody is generated by a hybridoma deposited with the DSMZ (Deutsche Sammlung von Mikroorganismen and Zellkulturen GmbH, Braunschweig) and having accession number DSM ACC3009. The generation of this antibody is described in present Examples 1 and 2 to which reference is made here.

The ability of this mutation specific antibody recognizing the R132H mutation to detect single tumor cells within otherwise inconspicuous tissue is of special interest. So far antibody binding of the above mentioned preferred antibody to any other than tumor cells was not detected and, therefore, single positive cells are regarded as unequivocal evidence for tumor. This feature is of major diagnostic interest for surgical specimens from small low grade astrocytomas or oligodendrogliomas frequently not containing solid tumor but rather tumor infiltrated brain tissue. The discrepancy between the mutation type observed in IDH1, namely heterozygous mutations restricted to a single codon in absence of other truncating mutations which is supportive for an activating mutation and the proven inactivation of dehydrogenase activity upon mutation suggest additional functions for wild type or mutant IDH1.

The term "antibody" as used herein relates to any type of antibody known in the art. An antibody as used herein includes intact immunoglobulin molecules, as well as fragments thereof, such as Fab, F(ab)$_2$, and Fv, which are capable of binding an epitope of IDH1. Typically, at least 6, 8, 10, or 12 contiguous amino acids are required to form an epitope. However, epitopes which involve non-contiguous amino acids may require more, e.g., at least 15, 25, or 50 amino acids.

An antibody which specifically binds to IDH1 or the mutated version of the protein can be used in immunochemical assays, such as Western blots, ELISAs, radioimmunoassays, immunohistochemical assays, immunoprecipitations, or other immunochemical assays known in the art. Various immunoassays can be used to identify antibodies having the desired specificity. Numerous protocols for competitive binding or immunoradiometric assays are well known in the art. Such immunoassays typically involve the measurement of complex formation between an immunogen and an antibody which specifically binds to the immunogen.

An antibody useful in the diagnostic method of the present invention can be raised according to well established methods, i.e., an IDH1 polypeptide can be used to immunize a mammal, such as a mouse, rat, rabbit, guinea pig, monkey, or human, to produce polyclonal antibodies. If desired, the (poly)peptide used as an immunogen can be conjugated to a carrier protein, such as bovine serum albumin, thyroglobulin, and keyhole limpet hemocyanin. Depending on the host species, various adjuvants can be used to increase the immunological response. Such adjuvants include, but are not limited to, Freund's adjuvant, mineral gels (e.g., aluminum hydroxide), and surface active substances (e.g. lysolecithin, pluronic polyols, polyanions, peptides, oil emulsions, keyhole limpet hemocyanin, and dinitrophenol). Among adjuvants used in humans, BCG (bacilli Calmette-Guerin) and *Corynebacterium parvum* are especially useful.

Monoclonal antibodies which specifically bind to IDH1 can be prepared using any technique which provides for the production of antibody molecules by continuous cell lines in culture. These techniques include, but are not limited to, the hybridoma technique, the human B cell hybridoma technique, and the EBV hybridoma technique [Kohler et al., Nature 256 (1985), 495-7).

Techniques described for the production of single chain antibodies can be adapted using methods known in the art to produce single chain antibodies which specifically bind to the IDH1 protein. Antibodies with related specificity, but of distinct idiotypic composition, can be generated by chain shuffling from random combinatorial immunoglobulin libraries [Burton, PNAS USA 88 (1991), 11120-3). Single-chain antibodies also can be constructed using a DNA amplification method, such as PCR, using hybridoma cDNA as a template [Thirion et al., Eur. J. Cancer Prev. 5 (1996), 507-11). Single-chain antibodies can be mono- or bispecific, and can be bivalent or tetravalent. Construction of tetravalent, bispecific single-chain antibodies is taught, for example, in Coloma & Morrison, Nat. Biotechnol. 15 (1997), 159-63). Construction of bivalent, bispecific single-chain antibodies is taught in Mallender & Voss, J. Biol. Chem. Xno9 (1994), 199-206).

A nucleotide sequence encoding a single-chain antibody can be constructed using manual or automated nucleotide synthesis, cloned into an expression construct using standard recombinant DNA methods, and introduced into a cell to express the coding sequence. Alternatively, single-chain antibodies can be produced directly using, for example, filamentous phage technology [Verhaar et al., Int. J. Cancer 61 (1995), 497-501).

Antibodies useful in a method of the invention can be purified by methods well known in the art. For example, antibodies can be affinity purified by protein-A protein-G column chromatography. The bound antibodies can then be eluted from the column using a buffer with a high salt concentration.

The invention is not limited to a particular immunoassay procedure, and therefore is intended to include both homogeneous and heterogeneous procedures. Exemplary immunoassays which can be conducted according to the invention include fluorescence polarisation immunoassay (FPIA), fluorescence immunoassay (FIA), enzyme immunoassay (EIA), nephelometric inhibition immunoassay (NIA), enzyme linked immunosorbent assay (ELISA), and radioimmunoassay (RIA). An indicator moiety, or label group, can be attached to the subject antibodies and is selected so as to meet the needs of various uses of the method which are often dictated by the availability of assay equipment and compatible immunoassay procedures. General techniques to be used in performing the various immunoassays noted above are known to those of ordinary skill in the art.

In the method of the present invention which relates to the selection of a therapy modality for a patient afflicted with a brain tumor the terms "therapy modality" or "mode of treatment" refer to a timely sequential or simultaneous administration of anti-tumor, and/or immune stimulating, and/or blood cell proliferative agents, and/or radiation therapy, and/or hyperthermia, and/or hypothermia for cancer therapy. The administration of these can be performed in an adjuvant and/or neoadjuvant mode. The composition of such "protocol" may vary in the dose of the single agent, timeframe of application and frequency of administration within a defined therapy window.

Thus, in a preferred embodiment of the method of the present invention the mode of treatment to be chosen (a) acts on cell proliferation, cell survival and/or cell motility, and/or (b) comprises administration of a chemotherapeutic agent.

In a more preferred embodiment, the mode of treatment comprises chemotherapy, administration of small molecule inhibitors, antibody based regimen, anti-proliferation regimen, pro-apoptotic regimen, pro-differentiation regimen, radiation and/or surgical therapy.

The knowledge of the presence or absence of the IDH1 mutation has an important influence on the therapeutic procedure. Currently, anaplastic astrocytomas WHO grade III are separated from glioblastomas WHO grade IV by the presence or absence of necrosis or vascular proliferation. However, the results of the NOA-04 study show that the prognosis of (histologically defined) anaplastic astrocytomas WHO grade III without IDH1 mutations is more or less identical to the prognosis of glioblastomas WHO grade IV.

In the therapy of malignant gliomas different protocols are applied to anaplastic astrocytomas WHO grade III and glioblastomas WHO grade IV. Later tumors are treated much more radical by combined radio- and chemotherapy whereas patients with anaplastic astrocytomas WHO grade III receive such bimodal therapy only if they are younger than 40 years of age. The IDH1 status allows the identification of those anaplastic astrocytomas WHO grade III that have a prognosis similar to glioblastomas WHO grade IV and that should be treated like such highest malignant brain tumors.

Furthermore, patients with an anaplastic astrocytoma WHO grade III without IDH1 mutation should be more frequently observed by a neuroradiologist in order to detect earlier the relapse. Instead, the interval for re-observations can be prolonged for patients with an anaplastic astrocytoma WHO grade III with IDH1 mutation.

The invention also provides a kit useful for carrying out a method of the invention, comprising an antibody that specifically binds to an IDH1 protein harbouring said mutation.

In a preferred embodiment, the kit comprises an antibody that has been raised using the peptide CKPIIGHHAYGD (SEQ ID NO: 1) as an immunogen. In a more preferred embodiment, the kit contains an antibody generated by the hybridoma deposited with the DSMZ (Deutsche Sammlung von Mikroorganismen and Zellkulturen GmbH) and having accession number DSM ACC3009.

As described in further detail in the examples, applicants also generated an antibody from another species recognizing both wild type and mutant IDH1 protein which allows simultaneous monitoring of the distribution of wild type and mutant protein for example by double immunofluorescence. The present set of antibodies will also allow testing for binding partners and detection of potential differences between wild type and mutant enzyme. In a preferred embodiment this antibody is contained in the above mentioned kit.

The following examples illustrate the invention and are not to be construed as limitations of the invention.

Example 1

Establishing an Antibody that Targets the IDH1 R132H Mutation (Quick Method)

The synthetic peptide CKPIIGHHAYGD (SEQ ID NO: 1) matching the IDH1 amino acid sequence from codon 125 to 137 and harbouring the R->H alteration was commercially generated. The Husar software package (DKFZ, Heidelberg, Germany) was used to select the appropriate sequence region. The peptide was conjugated with KLH (keyhole limpet hemocyanine). Six week old female C57 black sex mice (Charles River, Sulzfeld, Germany) were used. Always a 100 µL volume was injected in the hind limps of mice according to the following schedule:
Day 1: 20 µg CKPIIGHHAYGD (SEQ ID NO: 1) peptide linked to KLH dissolved in PBS elucidated 1:1 with complete Freund's Adjuvans was injected into the mice.
Day 2/3: 20 µg CKPIIGHHAYGD (SEQ ID NO: 1) peptide linked to KLH dissolved in PBS elucidated 1:1 with incomplete Freund's Adjuvans was injected into the mice.
Day 8: 20 µg CKPIIGHHAYGD (SEQ ID NO: 1) peptide linked to KLH dissolved in PBS elucidated 1:1 with incomplete Freund's Adjuvans was injected into the mice.
Day 11: 20 µg CKPIIGHHAYGD (SEQ ID NO: 1) peptide linked to KLH dissolved in PBS was injected into the mice.

Figure 1:
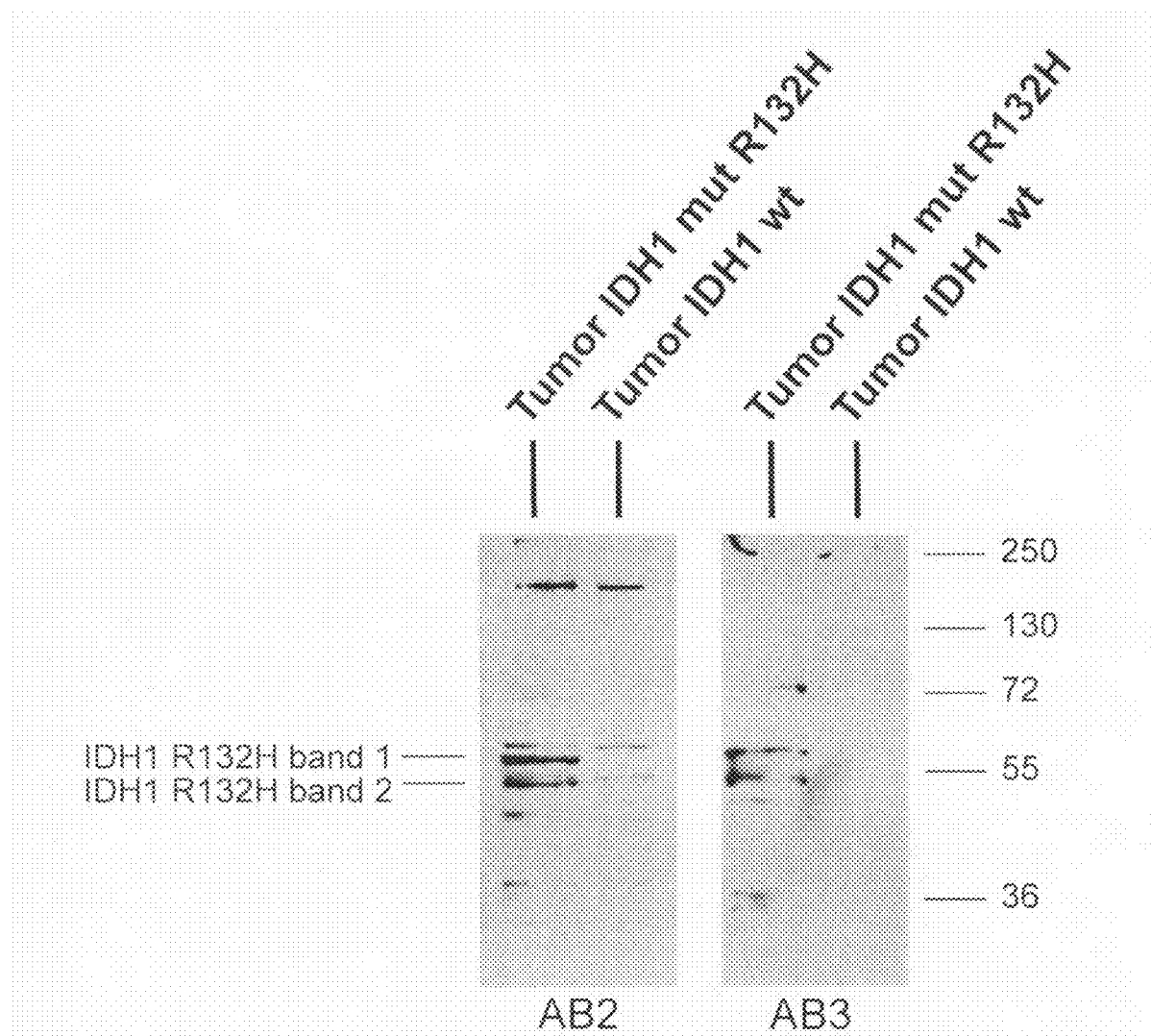
FIG. 1: Western blot using sera from two different immunized mice (AB2, AB3) against the R132H amino acid exchange. The protein extract of a tumor with an IDH1 mutation is seen in the left lane, in the right lane proteins from a tumor with IDH1 wild type are shown. Two bands of correct size are seen only in the lane with IDH1 R132H, indicating that these two mice produce antibodies that specifically detect the sequence alteration.

At day 12 extraction of blood from mice, separation of serum, western blot test against tumor proteins harbouring either the IDH1 R132H mutation or IDH1 wild type protein was carried out. Two mice that produce specific antibodies (AB2, AB3) were identified (FIG. 1).

At day 14 mice AB2 and AB3 were sacrificed. Popliteal lymph nodes were removed, cells separated and fused with tumor cells of the line SP2/0 to generate hybridoma cells. Finally, the hybridoma cells were grown, single cells were picked and separated to generate pure clones. Supernatants from clones were analyzed by western blot to detect the clones that produce IDH1 R132H specific antibodies.

Example 2

Establishing an Antibody that Targets the IDH1 R132H Mutation

The synthetic peptide CKPIIGHHAYGD (SEQ ID NO: 1) matching the IDH1 amino acid sequence from codon 125 to 137 and harbouring the R->H alteration was commercially generated. The Husar software package (DKFZ, Heidelberg, Germany) was used to select the appropriate sequence region. The peptide was conjugated with KLH (keyhole limpet hemocyanine). Six week old female C57 black sex mice (Charles River, Sulzfeld, Germany) were used.
All immunisations were made with:
20 µg Peptide-KLH in 50 µl PBS+20 µg QuieA (1 µg/µl; Quillaria saponaria; Gerbu, Gaiberg, Germany) in 50 µl PBS.

Always 50 µL of the above mentioned immunisation solution was injected in the hind limps of mice according to the following schedule:
Day 1: $1^{st}$ immunization
Day 4: $2^{nd}$ immunization
Day 8: $3^{rd}$ immunization
Day 11: $4^{th}$ immunization
Day 12: bleeding/testing
Day 116: $5^{th}$ immunization
Day 117: bleeding/testing At days 12 and 117 extraction of blood from mice, separation of serum, western blot test against tumor proteins harbouring either the IDH1 R132H mutation or IDH1 wild type protein was carried out. At day 120 mice were sacrificed. Popliteal lymph nodes were removed, cells separated and fused with tumor cells of the line SP2/0 to generate hybridoma cells. Finally, the hybridoma cells were grown, single cells were picked and separated to generate pure clones. Supernatants from clones were analyzed by western blot to detect the clones that produce IDH1 R132H specific antibodies. Concerning these above mentioned standard methods reference is made to "Harlow and Lane (1988) Antibodies: a laboratory manual. Cold Spring Harbour, New York: Cold Spring Harbor Laboratory)"

The mouse antibody producing hybridoma was deposited with the DSMZ (Deutsche Sammlung von Mikroorganismen and Zellkulturen GmbH, Braunschweig) on Oct. 2, 2009 and having accession number DSM ACC3009.

Analysis by Western blotting employing protein extracts from tumors with predetermined sequence status of IDH1 codon 132 demonstrates binding of the deposited R132H specific mouse clone mIDH1 R132H only in the extracts from three tumors carrying this mutation but not in those with other mutations or with wild type sequence. Thus, this antibody is highly useful for tumor classification, in detecting single infiltrating tumor cells and for the characterization of the cellular role of mutant IDH1 protein. The high specificity of mIDH1RI32H to detect single tumor cells is demonstrated in FIGS. 3G and H: Individual tumor cells bind antibody in the infiltrating edge towards cortex (G) and the white matter (H). The ability of the mutation specific antibody mIDH1R132H to detect single tumor cells within otherwise inconspicuous tissue is of special interest. So far antibody binding of mIDH1R132H to any other than tumor cells was not detected and, therefore, single positive cells are regarded as unequivocal evidence for tumor. This feature is of major diagnostic interest for surgical specimens from small low grade astrocytomas or oligodendrogliomas frequently not containing solid tumor but rather tumor infiltrated brain tissue. The discrepancy between the mutation type observed in IDH1, namely heterozygous mutations restricted to a single codon in absence of other truncating mutations which is supportive for an activating mutation and the proven inactivation of dehydrogenase activity upon mutation suggest additional functions for wild type or mutant IDH1.

Example 3

Establishing an Antibody that Targets the IDH1 R132H Mutation from Wistar Rats

In order to obtain an antibody from another species directed against wild type IDH1 Wistar rats were immunized with recombinant protein fused to a hexahistidine tag spanning the region of codon 244 to 594 of IDH1 (=antigen).

The rats were immunized by injection into their hind limps as follows:

Day 1: $1^{st}$ immunization with 100 µl immunization solution A

Day 8: $2^{nd}$ immunization with 100 µl immunization solution B

Day 12: $3^{rd}$ immunization with 100 µl immunization solution C

Day 21: 4th immunization with 100 µl immunization solution C

Day 22: bleeding/testing/fusion

Immunization solution A: 75 µg antigen in 100 µl PBS+100 µl FcA

Immunization solution B: 75 µg antigen in 100 µl PBS+100 µl FicA

Immunization solution C: 75 µg antigen in 200 µl PBS

At day 22 extraction of blood from the rats, separation of serum, western blot test against tumor proteins harbouring either the IDH1 R132H mutation or IDH1 wild type protein was carried out. At the same day rats were sacrificed. Popliteal lymph nodes were removed, cells separated and fused with tumor cells of the line SP2/0 to generate hybridoma cells. Finally, the hybridoma cells were grown, single cells were picked and separated to generate pure clones. Concerning these above mentioned standard methods reference is made to "Harlow and Lane (1988) Antibodies: a laboratory manual. Cold Spring Harbour, New York: Cold Spring Harbor Laboratory)"

Availability of this second antibody from another species recognizing both wild type and mutant IDH1 protein allows simultaneous monitoring of the distribution of wild type and mutant protein for example by double immunofluorescence.

Rat clone rIDH1 detected IDH1 protein in wild type tumors but also in tumors carrying different mutations due to its binding site distant from the motive including codon 132. Representative data is shown in FIGS. 3A and B. Immunohistochemistry with mIDH1 R132H in formalin fixed and paraffin embedded tumor tissues detected mutant protein only in tumors previously tested positive for the R132H mutation but not in tumors with other mutations in codon 132 or with wild type sequence. Antibody binding was restricted to tumor cells and did not occur in endothelial or lymphocytic cells. In contrast, rIDH 1 bound to all, tumor and non tumor cells. Representative data is shown in FIG. 3C to F.

The present set of antibodies will also allow testing for binding partners and detection of potential differences between wild type and mutant enzyme.

Example 4

Data that Support the Clinical Significance of IDH1 Mutations in Gliomas—Results of IDH1 Mutation Analysis using the Samples of the NOA-04 Study (Randomized Phase-III-Study of Sequential Radiochemotherapy of Oligoastrocytomas WHO Grade III using PCV or Temozolomide)

(A) To determine the different types of glioblastomas and their frequencies, more than 1000 diffuse gliomas were examined and IDH1 mutations with a frequency between 65% and 80% were detected in astrocytomas WHO grade II, anaplastic astrocytomas WHO grade III, oligodendrogliomas WHO grade II, anaplastic oligodendrogliomas WHO grade oligoastrocytomas WHO grade II and anaplastic oligoastrocytomas WHO grade III and secondary glioblastomas. However, in primary glioblastomas a mutation rate just as low as 5% was observed. Next, the potential of IDH1 as prognostic marker was analyzed. Therefore, different series consisting of glioblastomas, anaplastic gliomas and diffuse astrocytomas were investigated for IDH1 mutations and mutation status was correlated to patient survival. A highly significant association of IDHI mutation status and clinical outcome was found for malignant gliomas. However, a similar effect was not observed for diffuse astrocytomas. It is concluded that IDH1 mutations are the most frequent genetic alterations in diffuse gliomas WHO grade II and III and secondary glioblastomas, but not in primary glioblastomas, and, that IDH1 mutations have the potential as prognostic marker.

(B) A series of 209 anaplastic gliomas WHO grade III was analyzed for a mutation in exon 4 of IDH1 by DNA sequencing. This tumor panel consists of anaplastic astrocytomas WHO grade III, anaplastic oligoastrocytomas WHO grade III and anaplastic oligodendrogliomas WHO grade III. In summary, 136 tumors carried a mutation. In 129/136 samples (95%) the identified mutation was a heterozygous G395A mutations that results in an R132H amino acid exchange.

The correlation between the IDH1 status and the survival data showed that IDH1 mutations predict the biological behaviour of the gliomas. Patients with tumors that harbour an IDH1 mutation lived significantly longer than patients with IDH1 wild-type. This effect was observed for anaplastic astrocytic tumors and for anaplastic oligodendroglial tumors as well (FIG. 2).

While the many forms of the invention herein disclosed constitute presently preferred embodiments, many others are possible and further details of the preferred embodiments and other possible embodiments are not to be construed as limitations: It is understood that the terms used herein are merely descriptive rather than limiting and the various changes and many equivalents may be made without departing from the spirit or scope of the claimed invention.

The invention claimed is:

1. A method for the estimation of a prognosis for human patients having a brain tumor, comprising
  (a) obtaining a brain tumor sample from a patient; and
  (b) determining the presence of a mutation at position 132 of isocitrate dehydrogenase (IDH1) on the protein level using an antibody that can distinguish between an IDH1 protein harbouring said mutation and an unmutated version of the protein, wherein the mutation is R132H and wherein said antibody is raised using the peptide CKPIIGHHAYGD (SEQ ID NO: 1) as an immunogen and generated by a hybridoma having accession number DSM ACC3009; whereby a patient having a brain tumor and harbouring said mutation has a better prognosis than a patient without said mutation wherein the tumor is a glioma and selected from anaplastic astrocytoma WHO grade III, anaplastic oligoastrocytoma WHO grade III, and anaplastic oligodendroglioma grade III.

2. A method of selecting a therapy modality for a human patient afflicted with a brain tumor, comprising
  (a) obtaining a brain tumor sample from said patient; and
  (b) determining the presence of a mutation at position 132 of isocitrate dehydrogenase (IDH1) on the protein level using an antibody that can distinguish between an IDH1 protein harbouring said mutation and an unmutated version of the protein, wherein said antibody is raised using the peptide CKPIIGHHAYGD (SEQ ID NO: 1) as an immunogen and generated by a hybridoma having accession number DSM ACC3009; whereby the selection of a therapy modality for the patient afflicted with a brain tumor depends on the presence or absence of said mutation, wherein the tumor is glioma and selected from anaplastic astrocytoma WHO grade III, anaplastic oligoastrocytoma WHO grade III, and anaplastic oligodendroglioma grade III.

3. A method of diagnosing a brain tumor in a human patient suspected of having a brain tumor, comprising
  (a) obtaining a brain sample suspected of harboring a tumor from said patient; and
  (b) determining the presence of single tumor cells within otherwise inconspicuous tissue by using an antibody that specifically binds to an isocitrate dehydrogenase (IDH1) protein harbouring a mutation at position 132, wherein said antibody is raised using the peptide CKPIIGHHAYGD (SEQ ID NO: 1) as an immunogen and generated by a hybridoma having accession number DSM ACC3009.

4. The method of claim 3, wherein said brain tumor is a glioma.

5. The method of claim 2, wherein said therapy modality (a) acts on cell proliferation, cell survival and/or cell motility, and/or (b) comprises administration of a chemotherapeutic agent.

6. The method of claim 5, wherein the therapy (a) and/or (b) acts on angioneogenesis.

7. The method of claim 5, wherein said therapy modality comprises chemotherapy, administration of a small molecule inhibitor, antibody based regimen, anti-proliferation regimen, pro-apoptotic regimen, pro-differentiation regimen, radiation and/or surgical therapy.

8. An Antibody generated by a hybridoma deposited with the DSMZ and having accession number DSM ACC3009.

9. A kit useful for carrying out a method of claim 1, comprising an antibody that specifically binds to an IDH1 protein harbouring said mutation, wherein said antibody is generated by a hybridoma deposited with the DSMZ and having accession number DSM ACC3009.

* * * * *